United States Patent
Small

(10) Patent No.: US 7,981,026 B2
(45) Date of Patent: Jul. 19, 2011

(54) MEDICAL PROCEDURE DRAPE

(76) Inventor: Thomas James Small, Franklin, IN (US)

( * ) Notice: Subject to any disclaimer, the term of this patent is extended or adjusted under 35 U.S.C. 154(b) by 999 days.

(21) Appl. No.: 11/474,060

(22) Filed: Jun. 26, 2006

(65) Prior Publication Data

US 2007/0299302 A1 Dec. 27, 2007

(51) Int. Cl.
*A61B 1/00* (2006.01)

(52) U.S. Cl. ............... 600/102; 600/121; 128/849

(58) Field of Classification Search .............. 128/847, 128/849; 600/102, 121, 227, 228, 229
See application file for complete search history.

(56) References Cited

U.S. PATENT DOCUMENTS

| | | | | |
|---|---|---|---|---|
| 188,028 A | * | 3/1877 | Erlandson | 124/67 |
| 1,862,237 A | * | 6/1932 | Pepler | 108/49 |
| 4,417,710 A | * | 11/1983 | Adair | 248/51 |
| 4,553,538 A | | 11/1985 | Rafelson | |
| 4,586,498 A | * | 5/1986 | Morris | 128/853 |
| 5,299,582 A | * | 4/1994 | Potts | 128/846 |
| 5,322,072 A | * | 6/1994 | Harrison et al. | 128/849 |
| 5,341,821 A | * | 8/1994 | DeHart | 128/849 |
| 5,546,961 A | * | 8/1996 | Harrison | 128/849 |
| 5,592,952 A | * | 1/1997 | Bohn | 128/849 |
| 5,824,007 A | * | 10/1998 | Faraz et al. | 606/130 |
| 5,875,780 A | * | 3/1999 | Rodriguez | 128/849 |
| 6,716,163 B2 | * | 4/2004 | Muhanna et al. | 600/206 |
| 6,820,622 B1 | * | 11/2004 | Teves et al. | 128/849 |
| 7,255,310 B2 | * | 8/2007 | Niwa et al. | 248/75 |
| 7,591,269 B2 | * | 9/2009 | Small | 128/849 |
| 2006/0243285 A1 | * | 11/2006 | Small | 128/849 |

FOREIGN PATENT DOCUMENTS

WO WO 2005018438 A1 * 3/2005

* cited by examiner

*Primary Examiner* — Matthew J Kasztejna
(74) *Attorney, Agent, or Firm* — Taft Stettinius & Hollister LLP

(57) ABSTRACT

A medical procedure drape, for use during a diagnostic and therapeutic procedures performed on a patient supported by a patient cart, including a cover and a holder for the endoscope. The cover superimposes a portion of the patient and a portion of the patient cart. The endoscope holder is fixed to a boundary of the cover and extends above the level of the patient support surface on the patient cart. The endoscope holder retains and supports the endoscope during insertion and at other such times that the endoscopist may wish to set the endoscope aside to perform other tasks.

13 Claims, 6 Drawing Sheets

MEDICAL PROCEDURE DRAPE

FIELD OF THE INVENTION

This invention relates to a method and apparatus for use during a medical procedure and more particularity to a medical procedure drape for use during a medical procedure including esophagogastroduodenoscopy, with or without biopsy, polypectomy, esophageal dilatation, endoscopic photography, endoscopic ultrasound, fulgeration, coagulation, variceal injection or banding, stent placement, or endoscopic retrograde cholangiopancreatography.

BACKGROUND OF THE INVENTION

Upper Gastrointestinal Endoscopy (esophagogastroduodenoscopy, EGD) is a commonly used examination of the upper gastrointestinal tract employing a flexible fiberoptic endoscope. Other versions of the flexible Upper GI Endoscope are available for examination of the small intestine (enteroscopy), performing ERCP (Endoscopic retrograde Cholangiopancreatography), TEE (Transesophageal Echocardiography), esophageal and mediastinal ultrasonography. The basic instrument is 100 centimeters in length and is controlled by a handpiece that utilizes dials for altering the direction of the tip of the endoscope, and valves for controlling suction and air and water insufflation. An umbilical connects the handpiece of the instrument to a tower of electromechanical modules supplying suction, airflow, and water. An electronics package connected to the endoscope controls light and photography functions. The endoscope has an operating channel allowing the endoscopist to take biopsies and remove tissue from within the upper gastrointestinal tract.

The patient is brought to the endoscopy suite and the posterior oral pharynx is anesthetized with a topical anesthetic either swallowed or sprayed into the appropriate area. The patient is placed in the left lateral position with the head supported on a pillow. The patient is sedated or anesthetized with one of a variety of injectable agents administered in the intravenous access site. An appropriate drape is applied to the patient cart and to the patient in order to protect the patient, the environment, and the operator from any secretions from the upper GI tract during the procedure. An oral-pharyngeal suction cannula is available for assistance in keeping the mouth and the pharynx clear of secretions. The endoscope is brought up into the field and a bite block is used, if necessary, to prevent the patient from inadvertently biting the endoscope. The bite block is either placed between the incisors or placed on the shank of the endoscope for insertion between the incisors after the endoscope is placed in the esophagus. While the working end of the endoscope is inserted through the mouth and into the esophagus an assistant may hold the handpiece of the endoscope at the upper corner of the patient cart near the face of the patient, or the handpiece could be placed on the cart.

The problem arises that this employs the use of personnel who could be used elsewhere in the room to assist with other tasks. Placing the endoscope on the corner of the pillow or the patient cart can result in the endoscope sliding off of the cart and falling onto the floor while the endoscopist's attention is directed to the insertion of the endoscope into the patient's esophagus. Inadequate draping materials and methods frequently result in soiling and contamination of the patient, the patient cart, the endoscopist, and the endoscopy suite.

There is no specific item available to cover and protect the patient and the patient cart. Current practice consists of draping the patient with a disposable, movable plastic drape or a washable towel that is not impermeable to liquids. There is no specific item available to assist in managing the endoscope before, during, and after the endoscopy.

Soiling and contamination of the patient, the patient cart, the endoscopist, and the endoscopy suite environment can easily result without appropriate and adequate draping materials and methods. Clean-up is prolonged and timely transfer of the patient from the endoscopy suite is delayed by soiling and contamination. The utility and security of the endoscope is compromised by the lack of a secure holder for the endoscope during various stages of the procedure.

It is therefore an object of the invention to control secretions and eliminate soiling and contamination of the patient, the patient cart, the endoscopist, and the environment.

It is another object of the invention to support and protect the endoscope at various times during the procedure.

SUMMARY OF THE INVENTION

In accordance with the present invention, there is provided a medical procedure drape, for use during a diagnostic and possibly therapeutic procedure performed on a patient supported by a patient cart, including a cover and a holder for the endoscope. The cover superimposes a portion of the patient and a portion of the patient cart. The endoscope holder is fixed to a boundary of the cover and extends above the level of the patient support surface on the patient cart.

BRIEF DESCRIPTION OF THE DRAWINGS

A complete understanding of the present invention may be obtained by reference to the accompanying drawings, when considered in conjunction with the subsequent, detailed description, in which.

For purposes of clarity and brevity, like elements and components will bear the same designations and numbering throughout the Figures.

DESCRIPTION OF THE PREFERRED EMBODIMENT

Figure 1:
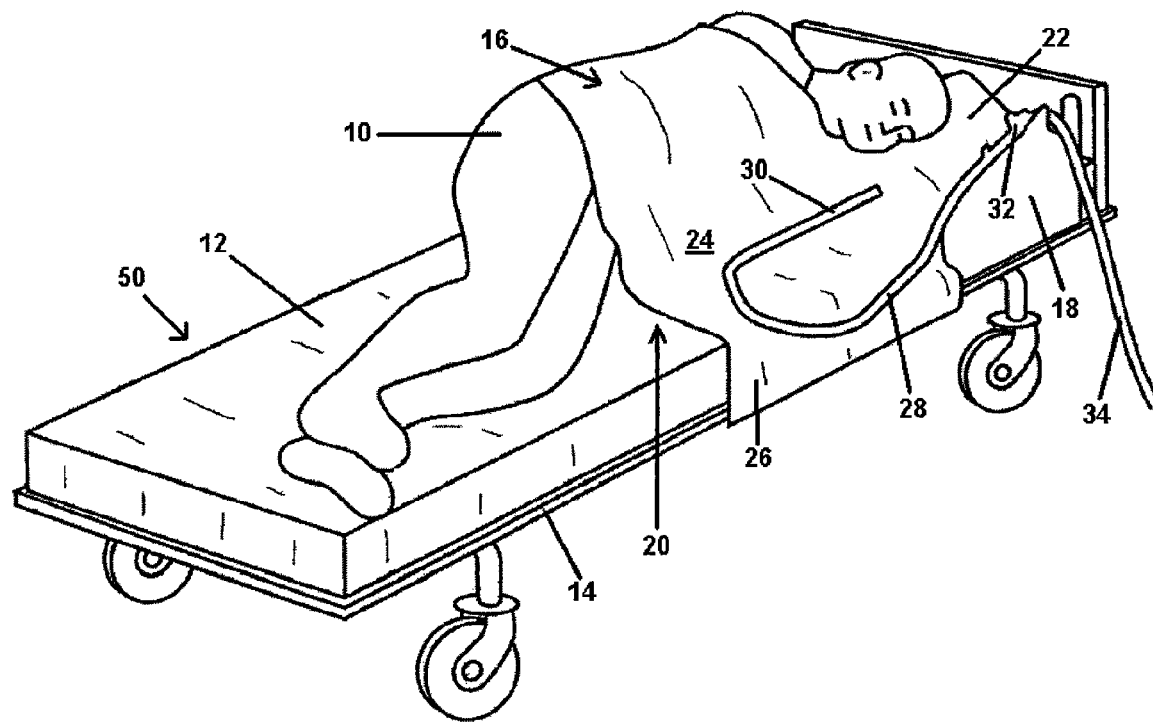
FIG. 1 is a perspective view of a patient positioned on the mattress of the patient cart ready to undergo an upper gi endoscopy with the flexible fiberoptic endoscope retained the endoscope holder.

FIG. 1 is a perspective view of a patient 10 positioned on the mattress of the patient cart 12 ready to undergo an upper GI endoscopy with the flexible fiberoptic endoscope 28 retained the endoscope holder 18.

Figure 2:
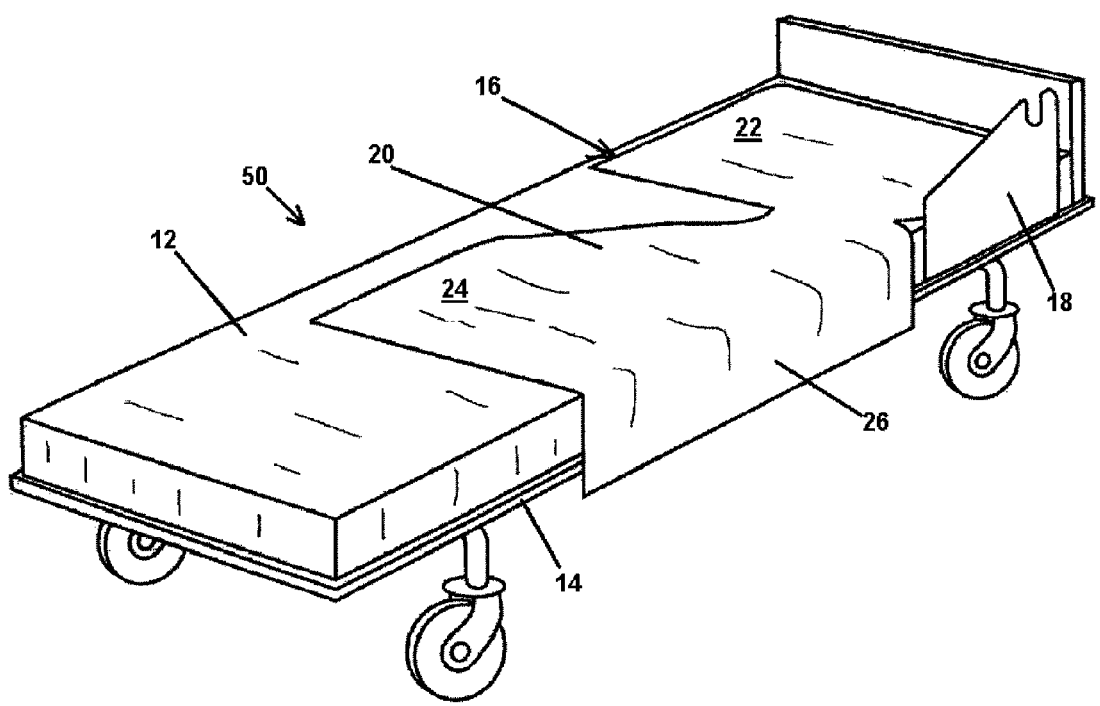
FIG. 2 is a perspective view of a patient cart with the cover of the medical procedure drape and the endoscope holder.

FIG. 2 is a perspective view of the patient cart 50 with the cover of the medical procedure drape 20 and the endoscope holder 18.

Figure 3:
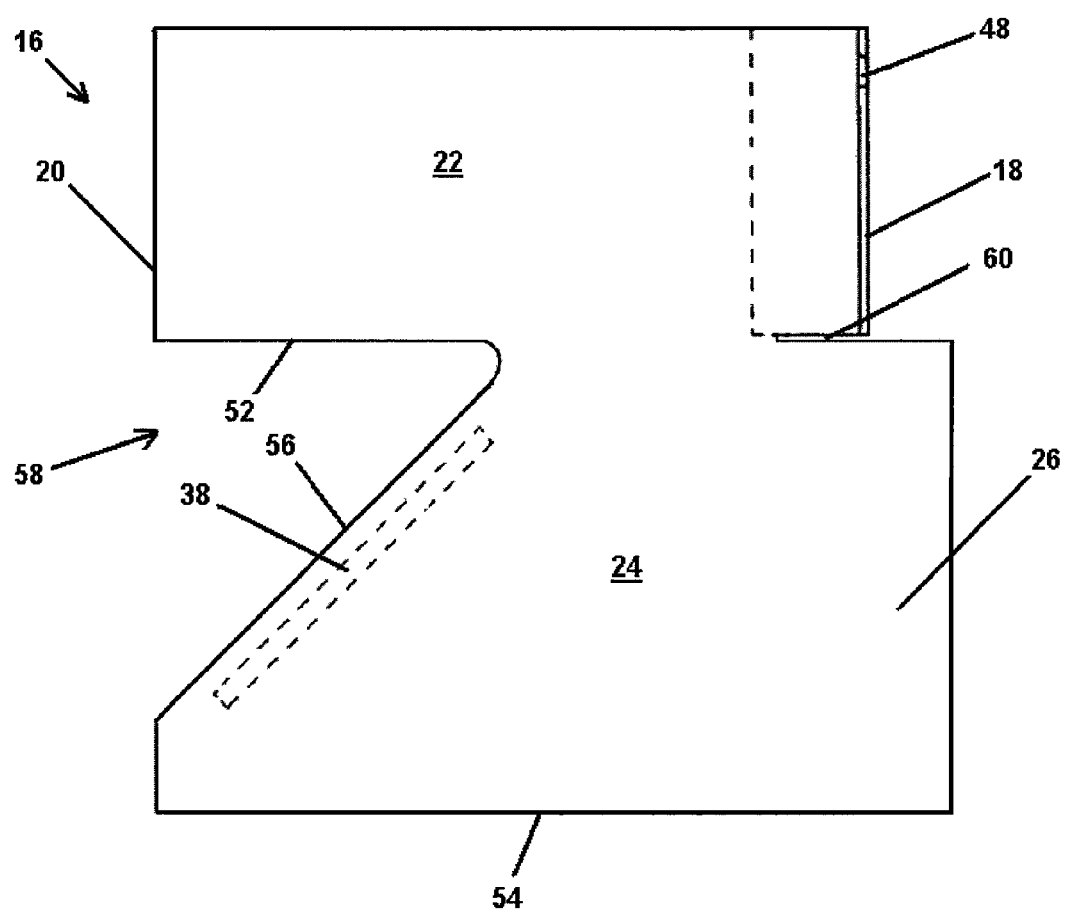
FIG. 3 is a plan view of a medical procedure drape including the cover and the endoscope holder.

FIG. 3 is a plan view of the medical procedure drape 16 and the endoscope holder 18.

Figure 4:
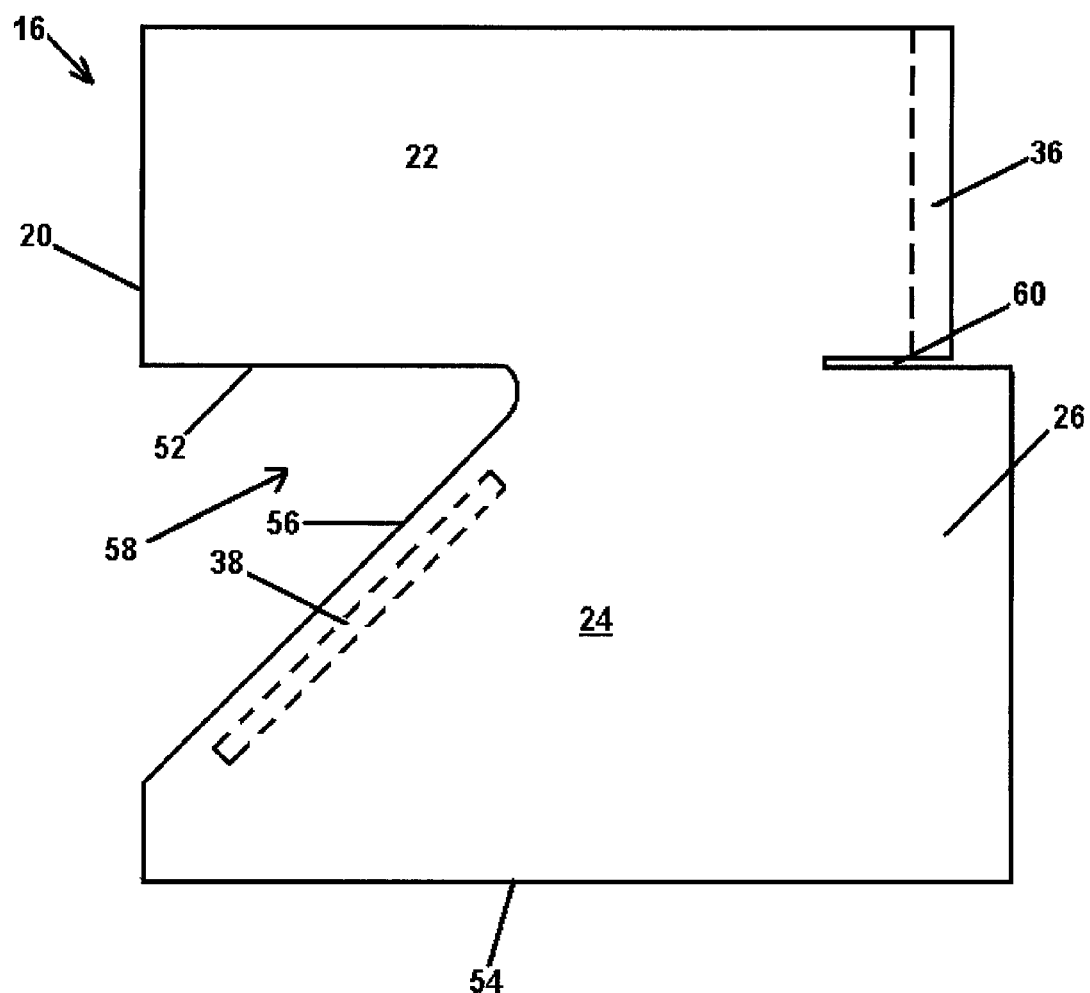
FIG. 4 is a plan view of a cover of a medical procedure drape in the present invention.

FIG. 4 is a plan view of the medical procedure drape 16 in the present invention.

Figure 5:
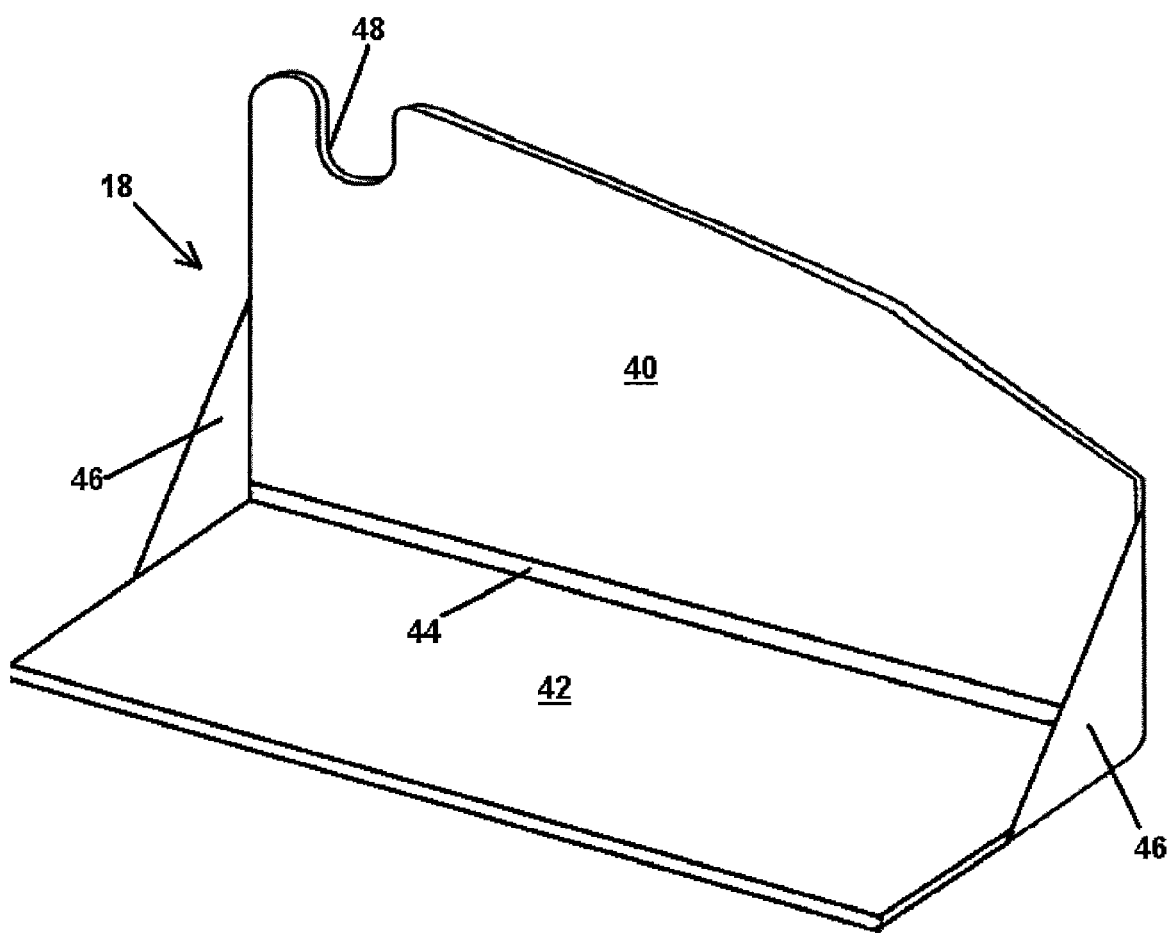
FIG. 5 is a perspective view of an endoscope holder of the present invention.

FIG. 5 is a perspective view of the endoscope holder 18 of the present invention.

Figure 6:
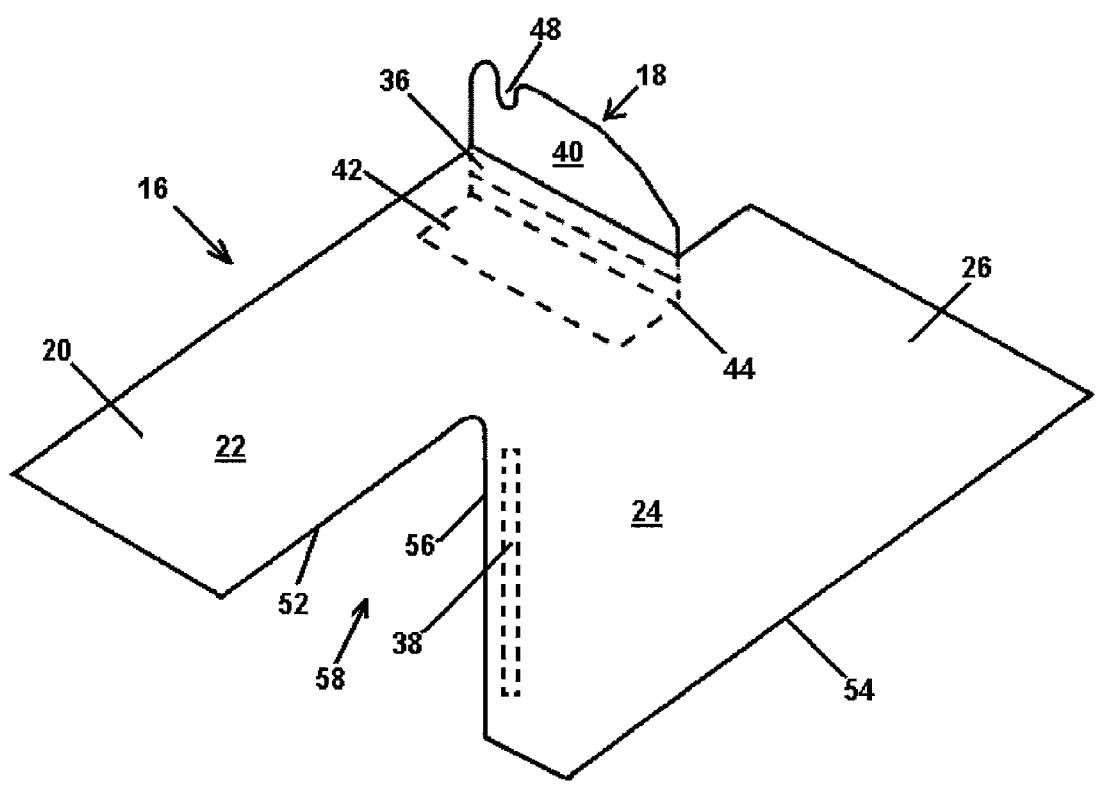
FIG. 6 is a perspective view of a medical procedure drape of FIG. 4 fixed to the endoscope holder of FIG. 5.

FIG. 6 is a perspective view of the medical procedure drape 16 of FIG. 4 fixed to the endoscope holder 18 of FIG. 5.

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Referring now to FIG. 1, there is shown a medical procedure drape 16 including a cover and an endoscope holder 18. During the procedure the patient 10 is sedated or anesthetized with intravenously administered medication while also having a topically applied anesthetic to the posterior oral pharynx. This may be accomplished by either swallowing a viscous liquid, or spraying a topical anesthetic directly on the mucosal surfaces of the posterior oral pharynx. The patient 10 is positioned on the patient cart 50 in the left lateral decubitus position with the head on a supportive pillow. The airway is protected by proper positioning to allow unobstructed spontaneous respiration and adequate pulmonary function.

The medical procedure drape 16 is positioned such that the cover of the medical procedure drape 20 will have the cephalad portion of the cover 22 superimpose the supportive pillow, while the caudal portion of the cover 24 superimposes the neck, chest, and arms of the patient 10. A free flap of the cover 26 hangs over the side of the mattress of the patient cart 12. The attached endoscope holder 18 is positioned so that the horizontal member 42 of the endoscope holder 18 is introduced between the mattress of the patient cart 12 and the deck of the patient cart 14. The vertical member 40 of the endoscope holder 18 is aligned with the side of the mattress of the patient cart 12.

The flexible fiberoptic endoscope 28 is positioned with the controlling handpiece of the endoscope 32 on the patient 10 side of the endoscope holder 18, having the umbilical of the endoscope 34 lying in the notch 48 of the endoscope holder 18. The working end of the endoscope 30 is lying on the cover of the medical procedure drape 20, on the horizontal surface of the mattress of the patient cart 12. This positions the working end of the endoscope 30 for manual insertion into the oral pharynx and esophagus of the patient 10. The endoscope holder 18 allows the endoscopist to utilize both hands for the insertion of the flexible fiberoptic endoscope 28 without the possibility of the controlling handpiece of the endoscope 32 falling off of the patient cart 50 and sustaining damage.

The endoscopist and the medical equipment cart containing light source, camera, suction, and air and water supplies are not depicted for clarity, and to demonstrate the detail and position of the medical procedure drape 16, the patient 10, and the patient cart 50.

FIG. 2 is a perspective view of the medical procedure drape 16, including the cover of the medical procedure drape 20 overlying the mattress of the patient cart 12, and the endoscope holder 18 inserted in position between the mattress of the patient cart 12 and the deck of the patient cart 14. The cephalad portion of the cover 22, the caudal portion of the cover 24, and the free flap of the cover 26 are demonstrated here. The relationship of the endoscope holder 18 and its location between the mattress of the patient cart 12 and the deck of the patient cart 14 are depicted. The patient 10, the flexible fiberoptic endoscope 28, and the pillow are omitted from this figure to depict the detail of this embodiment of the present invention.

FIG. 3 is a plan view of the medical procedure drape 16 including the cover of the medical procedure drape 20 and the endoscope holder 18. The cephalad portion of the cover 22 used to superimpose the pillow is seen directly opposite the endoscope holder 18. The cephalad portion of the cover 22 has an edge or side 52 that is disposed along the width of the support surface of the patient cart 50. The free flap of the cover 26 is the portion of the cover of the medical procedure drape 20 which hangs vertically over the edge of the mattress of the patient cart 12, thus protecting the patient cart 50. The caudal portion of the cover 24 superimposes the chest and arms of the patient 10 and a portion of the patient cart 50. The caudal portion of the cover 24 has an edge or side 54 that is disposed along the width of the support surface of the patient cart 50. The cephalad portion of the cover 22 and the caudal portion of the cover 24 are further defined by an angularly disposed edge or side 56 that is positioned between edges 52 and 54 and is configured to define a cut-out section 58 that can accommodate the neck of the patient 10. A cut-line 60 is also disposed along the width of the support surface of the patient cart 50 and specifically between the cephalad portion of the cover 22 and the free flap of the cover 26 to thereby allow the free flap to hang over the side of the patient support surface 50. An adhesive strip with peel-off paper backing 38 is located on the reverse side of the cover of the medical procedure drape 20 to cause the cover to adhere to the patient's chest and right arm.

FIG. 4 is a plan view of the cover of the medical procedure drape 20. The cover of the medical procedure drape 20 has an obverse side seen in this figure and a reverse side. It is constructed of a synthetic fabric which is flexible and impervious to liquids. Once again, as in FIG. 3, the cephalad portion of the cover 22, the caudal portion of the cover 24, and the free flap of the cover 26 are shown. Also shown is a flap of the cephalad of the cover 36 and is to accommodate adhesive attachment to the endoscope holder 18 as in FIG. 3.

On the reverse side of the cover of the medical procedure drape 20 is an adhesive strip with peel-off paper backing 38 to attach the caudal portion of the cover 24 to the patient 10.

FIG. 5 is a perspective view of the endoscope holder 18. The endoscope holder 18 can be constructed of rigid plastic, solid or corrugated cardboard. It is made up of two members, a vertical member 40 and a horizontal member 42. They are joined by a hinge 44 which may be made of the same material as the rigid members, or may be constructed of a flexible fabric. The hinge 44 allows the endoscope holder 18 to be folded flat, like a book, when closed. The motion is constrained, when fully open, to a right angle configuration by a gusset 46 at each end of the endoscope holder 18. The gusset 46 is constructed from a flexible fabric or tape material, adherent to each member.

The vertical member 40 has a notch 48 along the superior edge. It is shaped to accommodate the flexible fiberoptic endoscope 28 as depicted in FIG. 1. The caudal end of the endoscope holder 18 is tapered to a dimension approximating the thickness of the mattress of the patient cart 12.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims:

1. A draping system for use during a medical procedure, the draping system comprising:
 a cover having a first portion positionable across a section of a medical support surface that is configured to support a patient's head, the first portion further having a first edge that is disposed in a direction that is defined by a width of the medical support surface; and a second portion configured to cover at least a portion of a patient that is positioned on the medical support surface, the second portion having a flap that is adapted to hang over a side of the medical support surface and a second edge that is disposed in the direction defined by the width of the medical support, the second edge being substantially parallel to the first edge; and an instrument holder positioned substantially adjacent to the first portion of the cover and attached thereto by a strip of adhesive;

wherein the first and second portions of the cover are further defined by a third edge, the third edge being angularly disposed between the first edge and the second edge and defining a cut-out section between the first portion and the second portion, the cut-out section being configured to accommodate the neck of the patient, and wherein a cut line is defined between the first portion of the cover and the flap of the second portion of the cover, the cut line being disposed in a direction that is defined by the width of the medical support surface and being configured to allow the flap to hang over the side of the medical support surface.

2. The draping system of claim 1, wherein the cover is manufactured from a flexible material impervious to liquid.

3. The draping system of claim 1, wherein the instrument holder is an endoscope holder.

4. The draping system of claim 1, wherein the instrument holder includes a vertical member and a horizontal member, the vertical and horizontal members being hinged to one another in such a manner that the holder is positionable between an opened position and a closed position.

5. The draping system of claim 4, wherein the instrument holder, further comprises a gusset pair of gussets.

6. The draping system of claim 4, wherein the horizontal member has a top surface, the top surface being configured to mate against a bottom surface of the medical support surface when the instrument holder is attached thereto.

7. The draping system of claim 4, wherein the instrument holder further comprises a notch along a top portion of the vertical member, the notch being configured to hold an umbilical cord of an endoscope during a medical procedure.

8. The draping system of claim 1, wherein the second portion of the cover further includes a strip of adhesive for adhering the cover to the patient positioned on the medical support surface.

9. A draping system for use during a medical procedure, the draping system comprising:

a cover for a medical support surface including a cephalad portion having a first edge, a caudal portion having a second edge that is substantially parallel to the first edge, and a flap that is adapted to hang over a side of the medical support surface; and an instrument holder positioned substantially adjacent to the cephalad portion of the cover and attached thereto by a strip of adhesive, the instrument holder including a vertical member and a horizontal member, the vertical and horizontal members being hinged to one another in such a manner that the holder is positionable between an opened position and a closed position, the instrument holder further comprising a notch along a top portion of the vertical member, the notch being configured to hold a cord of a surgical instrument during the medical procedure;

wherein the cephalad portion and the caudal portion of the cover are further defined by a third edge, the third edge being angularly disposed between the first edge and the second edge and defining a cut-out section between the cephalad portion and the caudal portion, and wherein a cut line is defined between the cephalad portion of the cover and the flap of the cover, the cut line being disposed in a direction that is defined by the width of the medical support surface and being configured to allow the flap to hang over the side of the medical support surface.

10. The draping system of claim 9, wherein the cover is manufactured from a flexible material impervious to liquid.

11. The draping system of claim 9, wherein the instrument holder further comprises a gusset.

12. The draping system of claim 9, wherein the horizontal member has a top surface, the top surface being configured to mate against a bottom surface of the medical support surface when the instrument holder is attached thereto.

13. The draping system of claim 9, wherein the caudal portion of the cover further includes an adhesive material that is configured to adhere to a patient positioned on the medical support surface.

* * * * *

UNITED STATES PATENT AND TRADEMARK OFFICE
CERTIFICATE OF CORRECTION

| | | |
|---|---|---|
| PATENT NO. | : 7,981,026 B2 | Page 1 of 1 |
| APPLICATION NO. | : 11/474060 | |
| DATED | : July 19, 2011 | |
| INVENTOR(S) | : Thomas James Small | |

It is certified that error appears in the above-identified patent and that said Letters Patent is hereby corrected as shown below:

Column 5, Claim 5, line 36, delete the phrase "pair of gussets"

Signed and Sealed this
Thirtieth Day of August, 2011

David J. Kappos
*Director of the United States Patent and Trademark Office*